United States Patent
Dockrill et al.

(10) Patent No.: US 10,228,382 B2
(45) Date of Patent: Mar. 12, 2019

(54) FLUID TRANSPORT SYSTEM AND METHOD FOR TREATING ONE OR MORE TISSUE SAMPLES ON A SLIDE

(71) Applicant: LEICA BIOSYSTEMS MELBOURNE PTY LTD, Mt Waverly, Victoria (AU)

(72) Inventors: Mark Brian Dockrill, Chadstone (AU); Martin Limon, Richmond (AU); Michael Houston Drummond, Glen Waverley (AU); Mark Wilcock, Parkdale (AU); Brendyn Rodgers, Blackburn (AU)

(73) Assignee: LEICA BIOSYSTEMS MELBOURNE PTY LTD, Mount Waverly, Victoria (AU)

( * ) Notice: Subject to any disclaimer, the term of this patent is extended or adjusted under 35 U.S.C. 154(b) by 37 days.

(21) Appl. No.: 14/439,808

(22) PCT Filed: Nov. 1, 2013

(86) PCT No.: PCT/AU2013/001264
§ 371 (c)(1),
(2) Date: Apr. 30, 2015

(87) PCT Pub. No.: WO2014/066947
PCT Pub. Date: May 8, 2014

(65) Prior Publication Data
US 2015/0276772 A1    Oct. 1, 2015

Related U.S. Application Data

(60) Provisional application No. 61/721,269, filed on Nov. 1, 2012.

(51) Int. Cl.
*G01N 35/00* (2006.01)
*G01N 35/10* (2006.01)
*G01N 1/31* (2006.01)

(52) U.S. Cl.
CPC ....... *G01N 35/00029* (2013.01); *G01N 1/312* (2013.01); *G01N 35/0099* (2013.01);
(Continued)

(58) Field of Classification Search
CPC .............................. G01N 35/00; G01N 35/10
(Continued)

(56) References Cited

U.S. PATENT DOCUMENTS 3,495,926 A * 2/1970 Naz ........................ G01N 1/312
                                                                210/94
3,859,051 A * 1/1975 Natelson ............ G01N 35/1097
                                                                141/130

(Continued)

FOREIGN PATENT DOCUMENTS

JP    58163870 U    10/1983
JP    61202165 A     9/1986
(Continued)

OTHER PUBLICATIONS

International Search Report of PCT/AU2013/001264 dated Jan. 21, 2014 [PCT/ISA/210].
(Continued)

*Primary Examiner* — Arlen Soderquist
(74) *Attorney, Agent, or Firm* — Sughrue Mion, PLLC

(57) ABSTRACT

A fluid transport system for an automated slide treatment apparatus having slide treatment modules is disclosed. The fluid transport system including a fluid dispensing robot configured by a controller to dispense a plurality of reagents to slides received in the slide treatment modules. The fluid dispensing robot includes pumping means configured by the
(Continued)

controller to pump the reagents to be dispensed from a plurality of corresponding reagent containers; a probe having a body arranged to store one or more of the reagents pumped via the pumping means so as to prime the probe with said one or more of the reagents to be dispensed; and a well disposed on the body of the probe to store further of the reagents primed to be dispensed.

15 Claims, 11 Drawing Sheets

(52) U.S. Cl.
CPC ..... *G01N 35/1002* (2013.01); *G01N 35/1009* (2013.01); *G01N 2035/00138* (2013.01); *G01N 2035/1025* (2013.01)

(58) Field of Classification Search
USPC ................. 422/63–67, 509; 436/174, 180
See application file for complete search history.

(56) References Cited

U.S. PATENT DOCUMENTS

| | | | | |
|---|---|---|---|---|
| 3,915,652 | A * | 10/1975 | Natelson | B01L 9/065 141/130 |
| 4,730,631 | A * | 3/1988 | Schwartz | G01N 35/1004 134/155 |
| 4,794,085 | A * | 12/1988 | Jessop | G01N 35/1083 422/547 |
| 5,085,832 | A * | 2/1992 | Shaw | G01N 35/1083 422/547 |
| 5,158,748 | A * | 10/1992 | Obi | G01N 1/38 222/320 |
| 5,338,358 | A * | 8/1994 | Mizusawa | G01N 1/312 118/401 |
| 5,346,672 | A * | 9/1994 | Stapleton | B01L 3/5027 422/559 |
| 5,506,142 | A * | 4/1996 | Mahaffey | G01N 35/1004 422/547 |
| 5,578,270 | A * | 11/1996 | Reichler | B01L 3/502 422/510 |
| 5,725,831 | A * | 3/1998 | Reichler | B01L 3/502 422/417 |
| 5,783,148 | A * | 7/1998 | Cottingham | B01L 3/50273 422/417 |
| 6,060,320 | A * | 5/2000 | Dorenkott | G01N 35/1016 422/562 |
| 6,168,760 | B1 * | 1/2001 | Horn | B01L 3/5025 422/67 |
| 6,673,620 | B1 * | 1/2004 | Loeffler | B01L 3/502 359/398 |
| 7,569,381 | B2 * | 8/2009 | Aoyagi | B01L 3/502715 435/287.1 |
| 7,588,890 | B2 * | 9/2009 | Chu | B01D 11/0496 359/398 |
| 7,767,152 | B2 * | 8/2010 | Stead | B01L 3/502715 422/400 |
| 7,850,912 | B2 * | 12/2010 | Favuzzi | G01N 1/31 422/509 |
| 7,858,041 | B2 * | 12/2010 | Muraishi | B01L 3/021 422/511 |
| 8,486,335 | B2 * | 7/2013 | Angros | B01L 3/0293 422/63 |
| 8,600,142 | B2 * | 12/2013 | Berndt | G01N 1/30 382/128 |
| 2002/0182115 | A1 * | 12/2002 | Aghassi | G01N 1/312 422/400 |
| 2004/0037739 | A1 * | 2/2004 | McNeely | B01F 5/10 422/417 |
| 2004/0086428 | A1 * | 5/2004 | Loeffler | B01L 3/502 422/537 |
| 2005/0233367 | A1 * | 10/2005 | Chu | B01D 11/0496 435/6.15 |
| 2005/0281711 | A1 * | 12/2005 | Testa | B01L 3/508 422/400 |
| 2006/0105359 | A1 * | 5/2006 | Favuzzi | B01L 3/508 435/6.19 |
| 2006/0115381 | A1 * | 6/2006 | Kuno | B01F 11/0045 422/400 |
| 2006/0120921 | A1 * | 6/2006 | Elliot | B01L 3/545 422/63 |
| 2006/0148063 | A1 * | 7/2006 | Fauzzi | G01N 1/31 435/286.4 |
| 2006/0166371 | A1 * | 7/2006 | Testa | B01L 3/508 436/174 |
| 2006/0178776 | A1 * | 8/2006 | Feingold | G01N 35/0092 700/245 |
| 2008/0273918 | A1 * | 11/2008 | Linder | B01L 3/5027 403/31 |
| 2009/0110597 | A1 * | 4/2009 | Ljungmann | G01N 1/312 422/62 |
| 2009/0325309 | A1 | 12/2009 | Favuzzi et al. | |
| 2010/0028978 | A1 | 2/2010 | Angros | |
| 2010/0240021 | A1 * | 9/2010 | Berndt | G01N 1/30 435/3 |
| 2011/0306081 | A1 * | 12/2011 | Szita | B01L 3/502715 435/29 |
| 2012/0025521 | A1 * | 2/2012 | Baller | B01J 19/0093 285/328 |
| 2012/0201723 | A1 | 8/2012 | Loeffler et al. | |
| 2013/0287645 | A1 * | 10/2013 | Shaikh | B01L 3/5027 422/502 |
| 2014/0315256 | A1 * | 10/2014 | Dockrill | G01N 1/312 435/91.2 |
| 2014/0329270 | A1 * | 11/2014 | Favaloro | G01N 1/312 435/30 |
| 2015/0253225 | A1 * | 9/2015 | Ng | G01N 1/31 422/536 |
| 2015/0300931 | A1 * | 10/2015 | Dockrill | G01N 1/312 435/30 |

FOREIGN PATENT DOCUMENTS

| | | |
|---|---|---|
| JP | 03111035 A | 5/1991 |
| JP | 6508216 A | 9/1994 |
| JP | 06288879 A | 10/1994 |
| JP | 07218513 A | 8/1995 |
| JP | 10114394 A | 5/1998 |
| JP | 2005-024477 A | 1/2005 |
| JP | 2007-526479 A | 9/2007 |
| JP | 2009506300 A | 2/2009 |
| WO | 93/12432 A1 | 6/1993 |
| WO | 9845205 A2 | 10/1998 |
| WO | 2005/084263 A2 | 9/2005 |

OTHER PUBLICATIONS

Communication from the European Patent Office dated Jun. 20, 2016 in European Application No. 13850113.5.
Communication from the Australian Patent Office issued Nov. 21, 2016 in Australian Application No. 2013337608.
Communication from the Australian Patent Office issued Jan. 10, 2017 in Australian Application No. 2013337608.
Communication from the Chinese Patent Office issued Oct. 10, 2016 in Chinese Application No. 2013800690513.
Partial translation of communication dated Aug. 22, 2017, issued by the Japan Patent Office in corresponding Japanese Application No. 2015-540001.

* cited by examiner

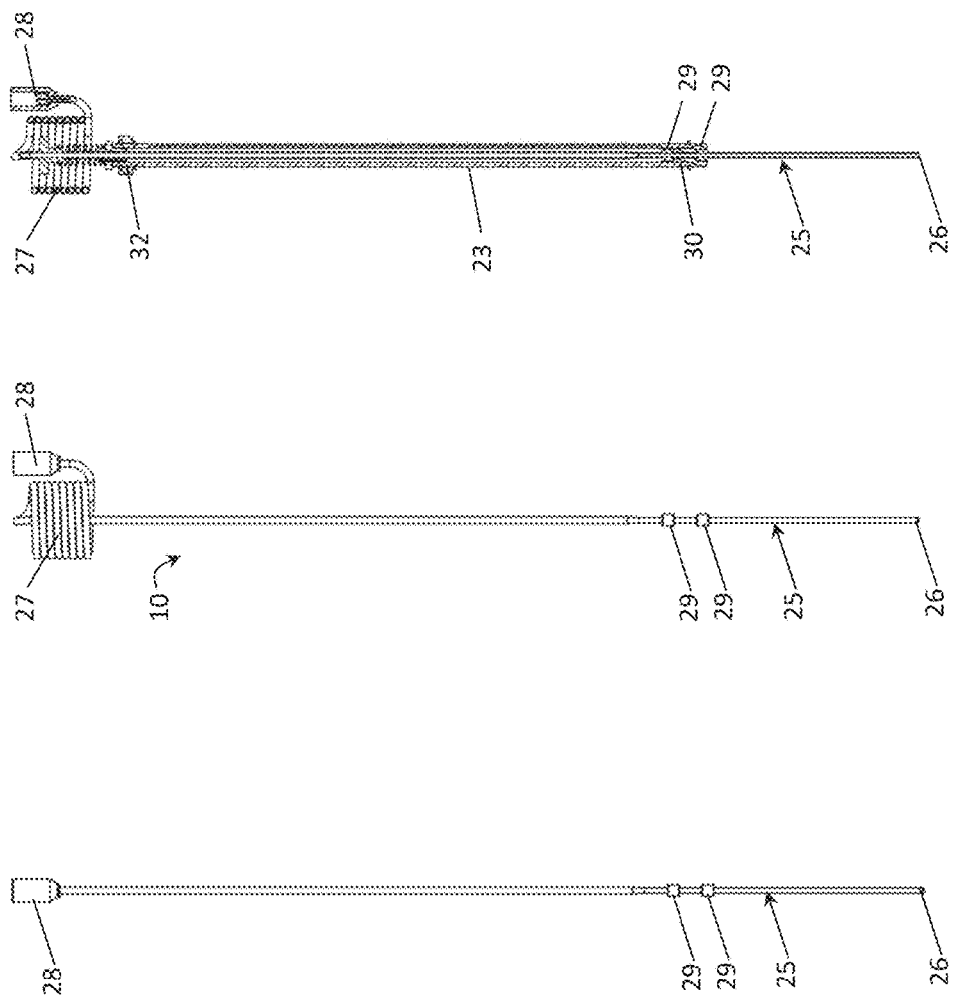

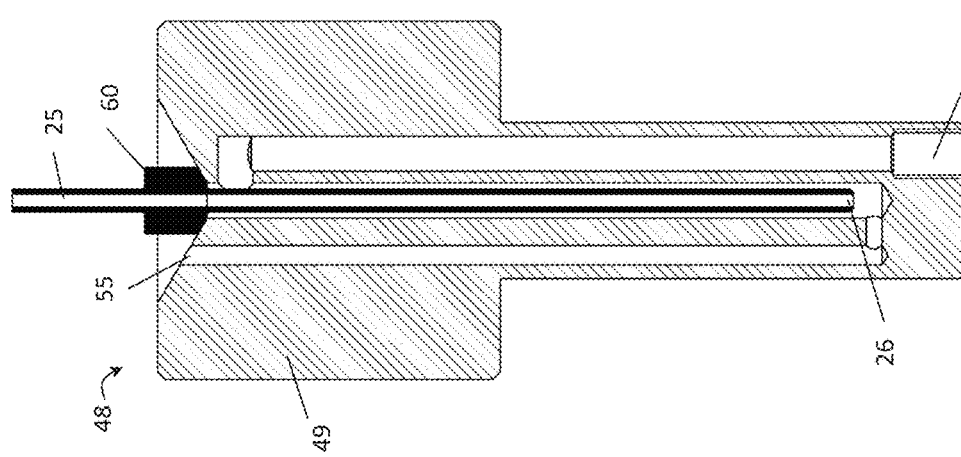
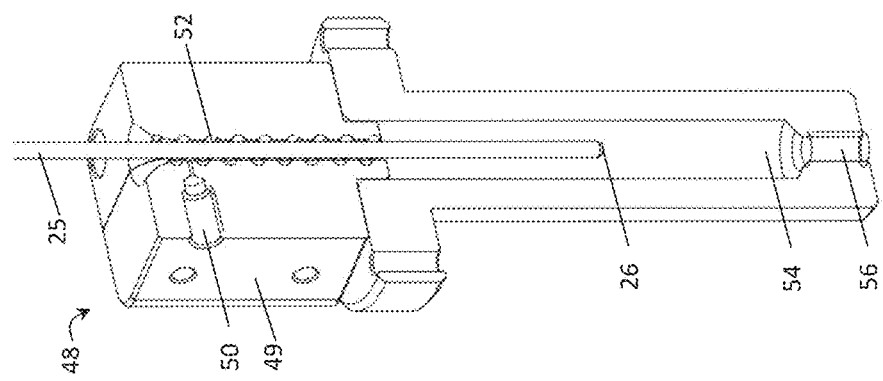

FLUID TRANSPORT SYSTEM AND METHOD FOR TREATING ONE OR MORE TISSUE SAMPLES ON A SLIDE

CROSS REFERENCE TO RELATED APPLICATIONS

This application is a National Stage of International Application No. PCT/AU2013/001264, filed Nov. 1, 2013, claiming priority based on U.S. Provisional Patent Application No. 61/721,269, filed Nov. 1, 2012, the contents of all of which are incorporated herein by reference in their entirety.

TECHNICAL FIELD

The present invention relates to a fluid transport system for an automated slide treatment apparatus for treating one or more tissue samples disposed on slides, whereby the slide treatment apparatus includes a plurality of slide treatment modules arranged to receive ones of the slides.

The present invention relates particularly, but not exclusively, to a fluid dispensing robot configured by a controller to dispense a plurality of reagents to the slides received in the slide treatment modules to treat the one or more tissue samples. Particularly, the fluid dispensing robot is a fluid transfer probe (FTP) robot, which includes a probe, having a body arranged to store one or more of the reagents pumped via a pumping means so as to prime the probe with the reagents to be dispensed, and a well, disposed on the body of the probe to store further of the reagents so as to increase a volume of the reagents primed to be dispensed. The one or more tissue samples on the slide can thus be treated when the probe dispenses the primed reagents to the slides received in the slide treatment modules.

BACKGROUND TO THE INVENTION

Existing tissue sample treatment methods, in some applications, comprise a number of steps that are performed manually. For example, in immunologic applications, such as in-situ hybridization (ISH) and immunohistochemical (IHC) applications, some steps, including baking a sample onto a slide, dewaxing, and epitope retrieval, are performed manually by an operator to treat the tissue sample before it can be used in a staining apparatus for staining the tissue sample according to a predetermined staining protocol.

Immunohistochemical staining and in situ nucleic acid analysis are tools used in histological diagnosis and the study of tissue morphology. Immunohistochemical staining relies on the specific binding affinity of antibodies with epitopes in tissue samples, and the increasing availability of antibodies which bind specifically with unique epitopes present only in certain types of diseased cellular tissue. Immunohistochemical staining involves a series of treatment steps conducted on a tissue sample (typically a section) mounted on a glass slide to highlight, by selective staining, certain morphological indicators of disease states.

Typical treatment steps include pre-treatment of the tissue sample to reduce non-specific binding, antibody treatment and incubation, enzyme labelled secondary antibody treatment and incubation, substrate reaction with the enzyme to produce a fluorophore or chromophore highlighting areas of the tissue sample having epitopes binding with the antibody, counterstaining, and the like. Between each treatment step, the tissue sample must be rinsed to remove unreacted residual reagent from the prior step. Most treatment steps involve a period of incubation typically conducted at ambient temperature of around 25° C. up to around 40° C., while cell conditioning steps are typically conducted at somewhat higher temperatures, e.g. 90° C. to 100° C. In-situ DNA analysis relies upon the specific binding affinity of probes (DNA binding proteins) with unique nucleotide sequences in cell or tissue samples and similarly involves a series of process steps, with a variety of reagents and process temperature requirements. Some specific reactions involve temperatures up to 120° C. to 130° C.

Attempts have been made to automatically treat tissue samples disposed on slides for immunologic applications using, for example, an automated tissue sample staining apparatus. In an existing example, the automated staining apparatus treats tissue samples using reagents to treat the sample before staining the samples on the slides. The treatment of the samples is performed automatically by one or more robots configured to dispense a plurality of designated reagents to slides in a predetermined sequence according to a staining protocol. In an existing example, the staining protocol uses high value reagents, such as antibodies, which are dispensed by a single robot in the staining apparatus one slide at a time. Due to the ever increasing numbers of histological test requests and biopsy samples, there are now significant pressures on laboratories to decrease turnaround time of treating tissue samples. Also, existing automated staining apparatuses tend to be bulky to accommodate the different treatment modules devoted to different treatment steps and thus take up a large amount of laboratory real estate.

SUMMARY

According to one aspect of the present invention, there is provided fluid transport system for an automated slide treatment apparatus for treating one or more tissue samples disposed on slides, the apparatus including a plurality of slide treatment modules arranged to receive ones of the slides, the fluid transport system including:
  a fluid dispensing robot configured by a controller to dispense a plurality of reagents to said ones of the slides received in the slide treatment modules to treat said one or more tissue samples respectively,
  wherein the fluid dispensing robot includes:
    a pumping means configured by the controller to pump the reagents to be dispensed from a plurality of corresponding reagent containers;
    a probe having a body arranged to store one or more of the reagents pumped via the pumping means so as to prime the probe with said one or more of the reagents to be dispensed; and
    a well disposed on the body of the probe and arranged to store further of said one or more of the reagents so as to increase a volume of the one or more of the reagents primed to be dispensed; wherein
    the probe is arranged to dispense said one or more of the reagents primed to be dispensed to said ones of the slides received in the slide treatment modules.

In an embodiment, the fluid dispensing robot includes a fluid transfer probe (FTP) robot. The FTP robot is configured by a controller to dispense a plurality of high value reagents to the slides in the slide treatment modules with the probe to treat the samples disposed thereon. It will be appreciated by those persons skilled in the art that the system can include more than one FTP robot. Also, it will be appreciated that the fluid dispensing robot can be configured by the controller to also dispense primed bulk reagents to the slides to treat the tissue samples disposed thereon.

In an embodiment, the pumping means is further configured by the controller to pump and/or aspirate more than one of the reagents from different ones of reagent containers successively with an air gap between successive reagents so as to prime the probe with a plurality of different reagents. That is, the probe, and the well, can be primed with different reagents to save the fluid dispensing robot the time required to aspirate the different reagents between dispenses. For example, the pumping means is a syringe pump arranged to aspirate different reagents from different containers into the probe with an air gap between successive reagents when the probe is inserted into the containers. The syringe pump can then dispense the primed different reagents to the same or different slides via movement of the fluid dispensing robot. Alternatively, the reagents can be aspirated and mixed in the probe for dispensing to slides.

The automated slide treatment apparatus also includes a slide transport robot including a slide handling head arranged to move a closure body of one of the slide treatment modules so as to move the closure body normally biased in a closed position to an open position when the slide transport robot is configured by the controller to move one of the slides to the slide treatment module for treatment by dispensing the primed reagents. The slide transport robot is described in the U.S. provisional patent application 61/721,269 entitled "Slide Transport System" having a filing date of 1 Nov. 2012, the contents of which are hereby incorporated herein by reference. In an embodiment, the slide transport robot and the fluid transport robot are combined in a gantry robot, which is configured to move in the x, y and z axes, to move the slides and to move the probe to the designated slide treatment modules to treat the slides located therein.

In an embodiment, the well includes a coiled tube. Also, preferably, the body of the probe includes an elongate tube and the coiled tube of the well is of a substantially similar diameter to the elongate tube of the body of the probe. In the embodiment, the coiled tubular well is disposed at an opposed end of the probe to a nozzle of the probe. It will be appreciated, however, that the well could be a tank or container to extend the volume of the probe, rather than a coiled tube, and it could be located at any point along the body of the probe.

Furthermore, in an embodiment, the coiled tube and the body of the probe are removeably attached to a reagent line connected to the pumping means at a resealable connector. The coiled tube and the body of the probe are preferably electrically isolated from the fluid dispensing robot at the resealable connector. Also, the body of the probe is removeably attached to the fluid dispensing robot at one or more probe collars. The probe collars may also made of an electrical insulating material, such as rubber or plastic, so the tube and the body of the probe is electrically isolated from the fluid dispensing robot at the one or more probe collars. In this way, the probe can be readily removed from the fluid dispensing robot for, say, cleaning or replacement of the probe.

Preferably, the fluid dispensing robot further includes a liquid level sensor for sensing an amount of dispensed reagent from the probe. In an example, the liquid level sensor is a capacitive liquid level sensor that detects an amount of fluid dispensed to the slide. In this case, the capacitive liquid level sensor is disposed on the electrically isolated probe described above to compare the effective capacitance of the probe when it is primed with reagents and after it has dispensed the reagents.

In addition, or in the alternative, the fluid dispensing robot includes a pressure sensor disposed between the well and the pumping means for sensing an amount of dispensed reagent from the probe. In the case where the fluid dispensing robot employs both the pressure sensor and the liquid level sensor to detect an amount of fluid dispensed to the slide, the pressure sensor is used to confirm the results of the liquid level sensor, and vice versa. Furthermore, the liquid level sensor can detect an amount of fluid aspirated to the probe to prime the probe for dispensing.

In an embodiment, the fluid dispensing robot includes a nozzle disposed at an end of the probe and arranged to dispense said one or more of the reagents primed to be dispensed. Preferably, the nozzle of the probe is arranged to couple with a cover member in one of the slide treatment modules and substantially sealingly mate with an inlet port of said cover member whilst said one or more reagents are being dispensed. The cover member, in an embodiment, forms a reaction chamber with the slide and the nozzle sealingly mates with the reaction chamber to dispense reagents to treat tissue samples on the slide. The cover member is described in the U.S. provisional patent application 61/721,280 entitled "Slide Staining Assembly and Cover Member" having a filing date of 1 Nov. 2012, the contents of which are hereby incorporated herein by reference.

In another embodiment, the fluid dispensing robot further includes a driver means to urge the nozzle of the probe towards the inlet port of said one of the slide treatment modules whilst the one or more reagents are being dispensed to maintain the seal with the inlet port.

In an embodiment, all or a part of the probe may be coated with a material that reduces frictions such as Teflon or ceramic. The material may be applied, or the probe prepared, by techniques such as electro-polishing.

In an embodiment, the fluid transport system further includes a wash station for washing the probe when the probe is inserted in a wash drum thereof. Preferably, the wash drum includes a wash fluid injection port connected to a wash pump of the fluid transport system, wherein the wash pump is configured by the controller to pump wash fluid into the wash drum from one or more wash fluid containers.

In an embodiment, the wash station may be positioned at any location including in close proximity to, or integral with, the fluid dispensing robot.

In an embodiment, the wash drum has a textured surface to create a turbulent flow of said wash fluid over the probe when inserted into the wash drum. Preferably, the textured surface includes spiral corrugations in the wash drum to create the turbulent flow of wash fluid over the inserted probe to wash the probe. It will be appreciated that other corrugations configurations in the wash drum could be employed by the system to create turbulent flow, such as space apart concentric rings. In any event, the wash drum may also include a collection chamber and scavenging port to collect and remove wash fluid from the wash drum.

In another embodiment, the wash drum comprises an inlet port and an outlet port whereby a gas is forced through the inlet port to mix with the wash fluid around the probe and the gas is forced out of the outlet port. For example, a vacuum means is arranged to apply a vacuum force to the outlet port to draw gas through the inlet port and out of the outlet port. In the example, the gas is air sucked into the wash drum from atmosphere through the inlet port.

In another embodiment, wash fluid is supplied via the probe reducing the need for a wash pump.

According to another aspect of the present invention, there is provided a method of transporting fluid for treatment of one or more tissue samples disposed on slides whereby ones of the slides are received in a plurality of slide treatment modules and a plurality of reagents are dispensed by at least one fluid dispensing robot to said ones of the slides received in the slide treatment modules to treat said one or more tissue samples respectively, the method including:

pumping the reagents to be dispensed from a plurality of corresponding reagent containers;

storing one or more of the reagents pumped from the corresponding reagent containers in a body of a probe so as to prime the probe with said one or more of the reagents to be dispensed;

further storing said one or more of the reagents in a well disposed on the body of the probe so as to increase a volume of the one or more of the reagents primed to be dispensed; and dispensing said one or more of the reagents primed to be dispensed to said ones of the slides received in the slide treatment modules.

According to another aspect of the present invention there is provided a computer program code which when executed by a controller implements the above method.

According to another aspect of the present invention there is provided a tangible computer medium comprising the above computer program code.

According to yet another aspect of the present invention there is provided a data file comprising the above program code.

BRIEF DESCRIPTION OF THE DRAWINGS

Embodiments of the present invention will now be described, by way of example only, with reference to the accompanying drawings, in which:

FIG. 5 is a front view of a probe of a fluid transport system according to an embodiment of the present invention;

FIG. 6 is a front view of a probe of a fluid transport system according to an embodiment of the present invention;

FIG. 7 is a sectional view of a probe of a fluid transport system according to an embodiment of the present invention;

FIG. 12A is a sectional view of a wash station of an automated slide treatment apparatus according to an embodiment of the present invention;

FIG. 12B is a sectional view of another wash station of an automated slide treatment apparatus according to an embodiment of the present invention;

DETAILED DESCRIPTION

Figure 1:
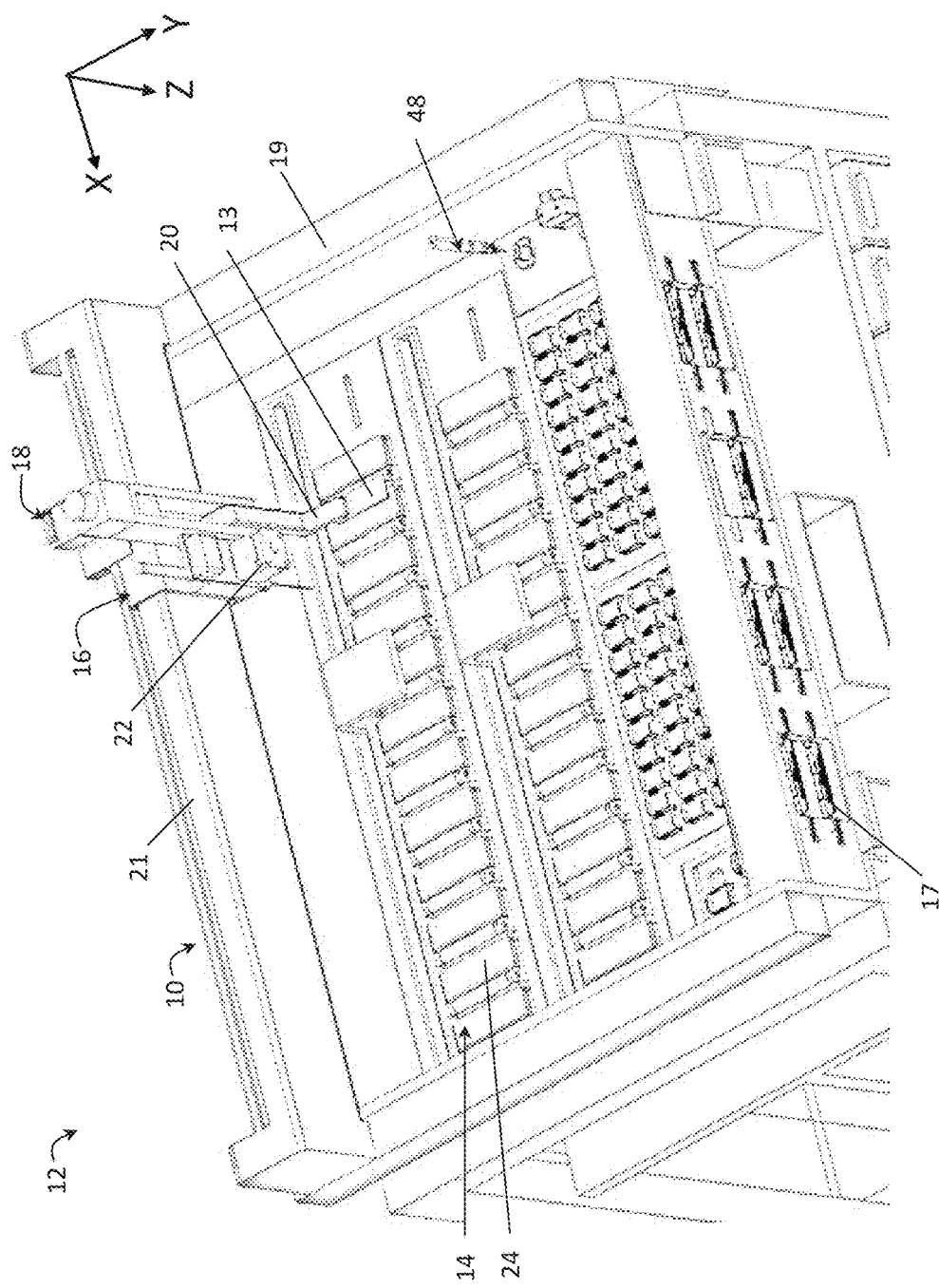
FIG. 1 is a perspective view of an automated slide treatment apparatus having a fluid transport system according to an embodiment of the present invention.

A fluid transport system 10 for an automated slide treatment apparatus 12 for treating tissue samples disposed on slides 13 is shown in FIG. 1. It can be seen that the slide treatment apparatus 12 includes a plurality of slide treatment modules 14 arranged to receive the slides 13, and includes at least one slide transport robot 18, in the form of a gantry robot configured by a controller, to move the slides 13 to and from the slide treatment modules 14. The fluid transport system 10 includes a fluid dispensing robot 16 configured by the controller to move to designated slide treatment module 14 to dispense a plurality of reagents to the slides 13 received in the slide treatment modules 14 to treat the tissue samples on the slides 13.

In the embodiment shown in the Figures, the slide transport robot 18 is combined with the fluid dispensing robot 16 in a gantry robot, which is configured to move in the x, y and z axes. It will be appreciated by those persons skilled in the art that the slide transport robot 18 can be separate from the fluid dispensing robot 16. For example, the slide transport robot 18 is an articulated armed robot while the fluid dispensing robot 16 is a gantry robot, and vice versa. In the embodiment, however, the fluid dispensing robot 16 includes a fluid transfer probe (FTP) robot configured by the controller to dispense a plurality of high value reagents stored in reagent containers to the slides 13 in the slide treatment modules 14. Examples of high value reagents include chromogens and antibodies. That is, the gantry robot includes the combined FTP robot 16 and the slide transport robot 18 to minimise the size and complexity of the apparatus 12. In any event, the x axis is a length of the apparatus 12, the y axis is a width of the apparatus 12 and the z axis corresponds to a height of the apparatus 12.

As described, the fluid dispensing robot 16, hereinafter referred to as FTP robot 16, and the slide transport robot 18 are configured by the controller to dispense reagents to slides in the slide treatment modules 14 and to move the slides 13 to and from the slide treatment modules 14. It will be appreciated by those persons skilled in the art that the controller of the automated slide treatment apparatus 12—and the slide transport robot 18 and the FTP robot 16—can either be implemented remotely from the apparatus 12 or can be implemented locally with respect to the apparatus 12. In any case, it will also be appreciated that the controller includes a number of modules, implemented by a processor and a memory for storing instructions for the modules, to provide instructions to the slide transport robot 18 and the FTP 16 to control movement thereof and dispensing of reagents.

As will be appreciated, the slide transport robot 18 is configured by the controller to move quickly between the different modules in the apparatus 12 in the three axes so as to efficiently move slides in and out of the slide treatment modules 14 so as to treat samples disposed on the slides in the slide treatment modules 14. For example, the slide transport robot 18 is configured to move from one corner of the apparatus 12 to the diagonally opposite corner in 2.2 seconds (which represents the maximum move with respect to the apparatus 12). The travel profiles for the slide transport robot 18 shown with respect to the apparatus 12 in FIG. 1 may be e.g. 780 mm in the x axis, 500 mm in the y axis and 120 mm in the z axis although these ranges are examples only.

It can also be seen that the gantry robot 18, and the FTP robot 16, moves along a rail 21 in the x direction and a rail 19 in the y direction so as to move slides to and from the slide treatment modules 14 and to dispense reagents to the slides 13 in the designated slide treatment modules 14 to treat those samples disposed on the slides.

Figure 2:
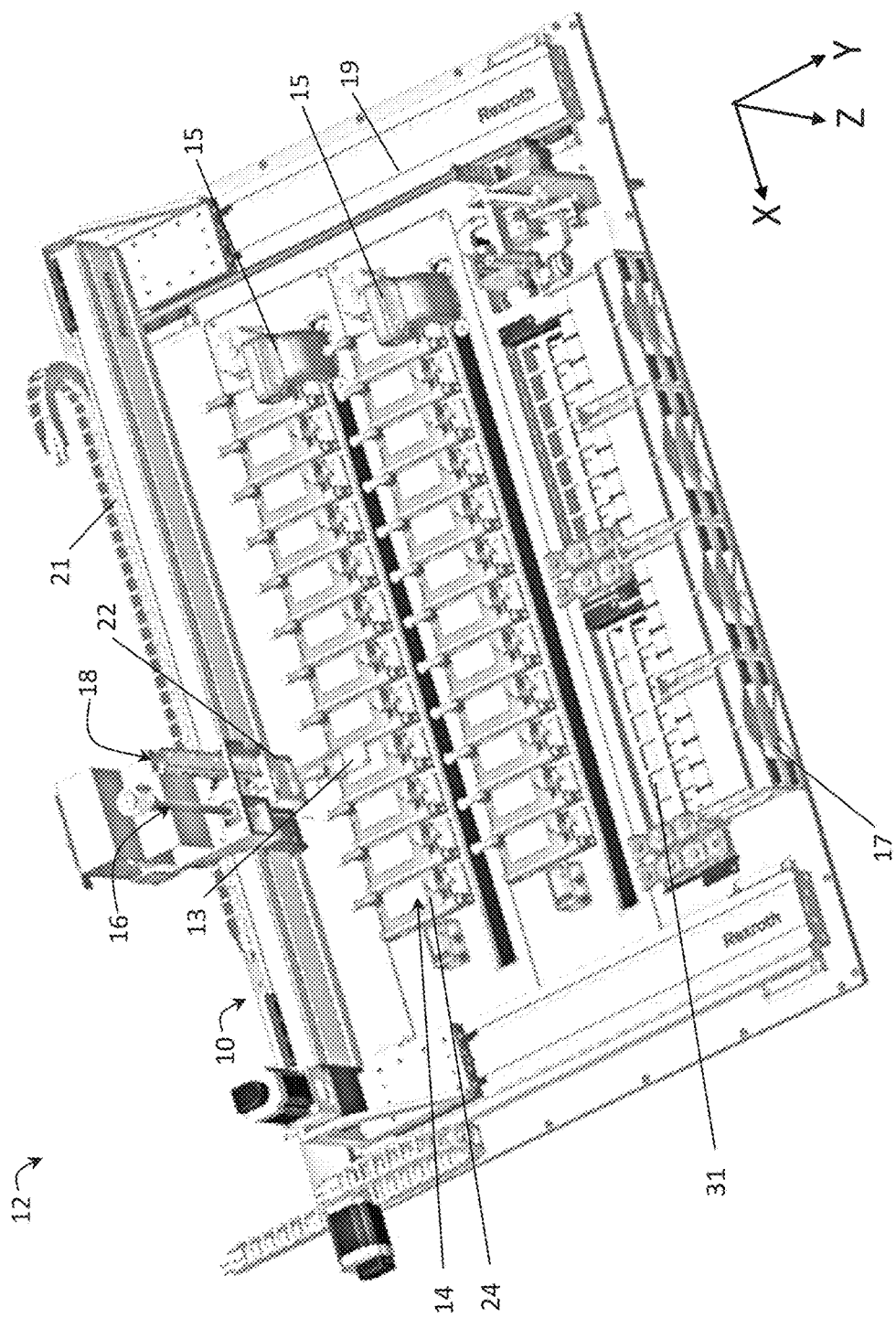
FIG. 2 is a further perspective view of an automated slide treatment apparatus having a fluid transport system according to an embodiment of the present invention.

As shown in the embodiment of FIG. 2, the apparatus 12 includes two bulk fluid robots (BFRs) 15 configured by the controller to dispense a plurality of lesser value reagents stored in reagent containers to the slides 13 received in the slide treatment modules 14 to also treat tissue samples on the slides. That is, in some cases, to treat the tissue samples on the slides 13, a designated combination and order of high and lesser value, bulk reagents is dispensed to a slide. It will be appreciated by those persons skilled in the art that the apparatus 12 may include more than two BFRs to dispense the lesser value reagents stored in reagent containers to the slides 13.

For example, the BFRs 15 are configured by the controller to dispense bulk reagents to the slides 13, such as oxalic acid, sulphuric acid, potassium permanganate, alcohol, dewaxing agent, haematoxylin, peroxide, citric acid, EDTA, DI water and Bond™ wash to treat the tissue samples disposed thereon. It can also be seen in FIG. 2 that there is a BFR 15 for each row of slide treatment modules 14 and that the slide transport robot 18 is configured to move the slides 13 to and from the slide treatment modules 14 without interfering with the BFRs 15 as the slide transport robot can move in the z direction. Indeed, in this case, the BFRs 15 are configured to move only in the x and z directions to dispense the bulk reagents to the slides 13 in the slide treatment modules 14.

Figure 3:
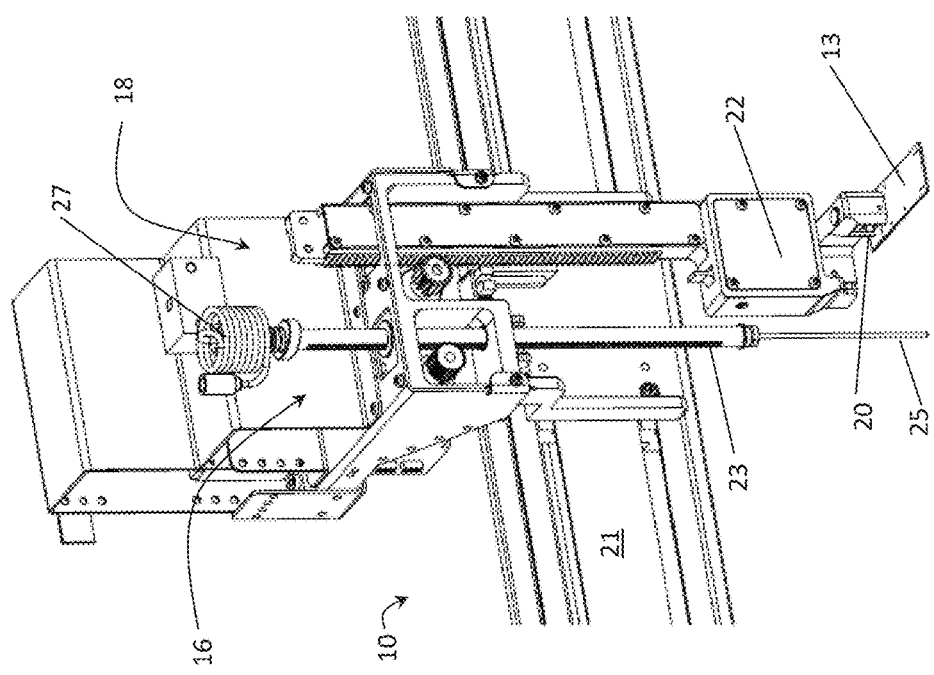
FIG. 3 is a perspective view of a fluid transport system for an automated slide treatment apparatus according to an embodiment of the present invention.

The slide transport robot 18 also includes a slide transport device 20, shown in FIG. 3, disposed on the slide transport robot 18, which is configured by the controller to releasably hold the slides 13. For example, the slide transport device 20 is a suction cup arranged to releasably hold the slide 13 when it is to be moved to a slide treatment module 14 and to release the slide 13 to locate it in a slide treatment module 14. The slide transport device 20 is also envisaged to include other means for releasably holding a slide, such as a gripper. Furthermore, in an embodiment, the slide transport robot 18 includes a slide handling head 22 arranged to move a closure body 24 of one of the slide treatment modules 14 so as to move the closure body 24 normally biased in a closed position to an open position when the slide transport robot is configured by the controller to move one of the slides 13 to the slide treatment module 14. The slide transport device 20 also extends from the slide handling head 22 and is configured by a controller to release the slide 13 so as to locate the slide in the slide treatment module 14 when the closure body 24 is held in the open position. The FTP robot 16 can then dispense reagents to the slide 13 when the closure body 24 of the slide treatment module 14 reverts back to the closed position after the slide handling head 22 moves in the x axis so as to close the closure body 24. As described, the slide transport robot 18 is described in more detail in the co-pending U.S. provisional patent application entitled "A Slide Transport System".

In use, the FTP robot 16 forces fluid into or withdraws fluid from a reaction chamber to achieve agitation and/or evacuation of reagent from the reaction chamber. Agitation can facilitate mixing of reagent and/or assist with bubble management within the reaction chamber during a processing step, increasing the likelihood of reagent contacting a sample on the substrate despite the existence of bubbles in the chamber. Reagent dispensing and withdrawal may be coupled with a pressure and/or vacuum or other source configured to apply negative and/or positive fluid pressures.

FIGS. 1 and 2 also show the automated slide treatment apparatus 12 having input and output buffer modules 17, whereby the input buffer module 17 introduces slides 13 to the apparatus 12 for treatment and the output buffer module 17 allows for the removal of the slides from the apparatus 12 after treatment of the tissue samples on the slides 13. The slide transport robot 18 of the embodiment shown in these figures is thus further configured to retrieve a slide from the input module 17 and locate it in a slide treatment module 14 and to remove the slide 13 from the slide treatment module 14 and locate it in the output module 17 after the tissue samples disposed on the slide have been treated with the FTP robot 16 and/or the BFR 15. In addition, the slide transport robot 18 of the embodiment can also be configured to move the slide to/from other modules (not shown) for performing other operations on the slide, such as coverslipping and digital imaging modules, before moving the slide to the output module.

Figure 4:
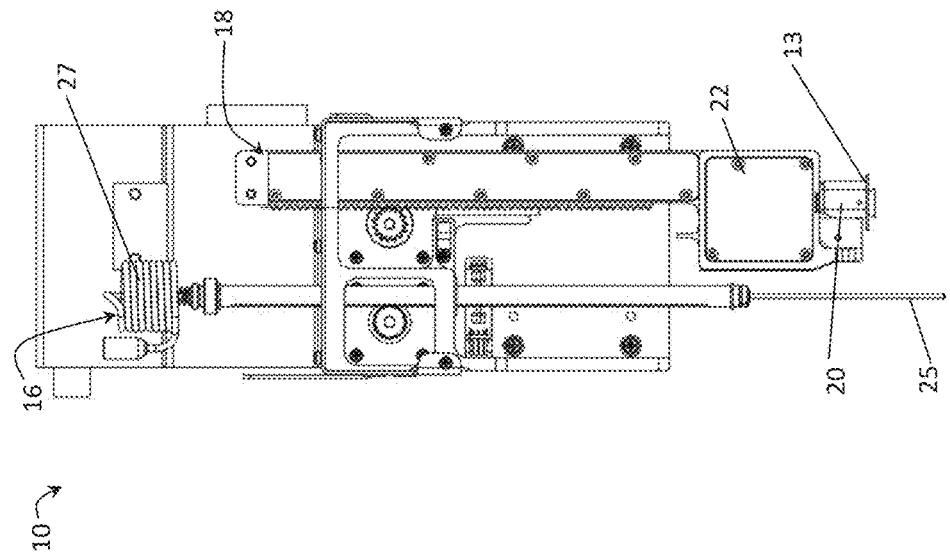
FIG. 4 is a side view of the fluid transport system of FIG. 3.

FIGS. 3 and 4 show the FTP robot 16 in further detail. The FTP robot 16 is configured to move along the rail 21 in the x axis and along a rack 23 in the z axis so as to locate a probe 25 of the fluid dispensing robot 16 at the designated slide treatment module 14 to dispense the designated reagents to the slide 13 received in the designated slide treatment module 14. The rack 23 is driven by a pinion on the FTP robot 16 to lower and raise the probe 25 in the z axis. That is, the probe 25 can be raised or lowered in the z axis so that the reagents can be dispensed to the slide 13 in the slide treatment module 14 when the closure body 24 of the slide treatment module 14 is in the closed position. In the embodiment, the FTP robot 16 moves along the rail 21 and the rail 19 in the x and y axes using a chain drive system driven by stepper motors. Nonetheless, it will be appreciated by those persons skilled in the art that other drive systems may be employed, such as another further rack and pinion or belt drive system, pneumatic, solenoid, or leadscrew systems.

The FTP robot 16 includes a pumping means (not shown) configured by the controller to pump reagents to be dispensed from a plurality of corresponding reagent containers by the probe 25 of the FTP robot 16. In one embodiment, the pumping means is a syringe pump configured to aspirate the reagents from the reagent containers to be dispensed. FIG. 2 shows a plurality of high value reagent containers 31 storing high value reagents for dispensing. It will be appreciated by those persons skilled in the art that the pumping means can be located on the FTP robot 16 or somewhere else on the apparatus 12. In an example, the syringe pumping means aspirates and dispenses high value reagents to/from a nozzle 26 disposed at one end of the probe 25 of the FTP robot 16 from the high value reagent containers 31. That is, the nozzle 26 is lowered by the stepper motor on the rack 23 of the FTP robot 16 into the designated reagent containers so that the reagents can be aspirated via action of the pumping means into the probe 25. It will be appreciated by persons skilled in the art that the sequence of aspirating and dispensing reagents is predetermined to treat the particular tissue samples disposed on the slides.

The probe 25 of the FTP robot 16 has an elongated body arranged to store one or more of the reagents pumped via the pumping means so as to prime the probe with the reagents to be dispensed. Thus, in use, the reagents are pumped to the probe 25 of the FTP robot 16 to be dispensed to one or more slides 13 in different slide treatment modules 14. Furthermore, the FTP robot 16 has a well 27, disposed on the body of the probe 25, arranged to store further of the reagents so as to increase a volume of the reagents primed to be dispensed. In this way, the probe 25 dispenses the primed reagents to a number of designated slides 13 received in designated slide treatment modules 14 without having to further aspirate and pump reagents into the probe 25. That is, without having to move the nozzle 26 of the probe 25 back to the high value reagent containers to prime the probe 25 and the well 27 again.

In addition, the pumping means can be further configured by the controller to pump and/or aspirate more than one of the reagents from different ones of reagent containers successively with an air gap between successive reagents so as to prime the probe with a plurality of different reagents. In this way, the FTP 16 robot can dispense different reagents to the same or different slides at different stages of their slide treatment protocol without having to return to the reagent containers 31 to aspirate further reagents.

Furthermore, it can be seen from the Figures that the nozzle 26 of the probe 25 is located adjacent the slide handling head 22 of the slide transport robot 18, which is arranged to contact against a bearing surface of the closure body 24 of a slide treatment module 14 to move the closure body 24 to the open position so that a slide 13 can be located therein for treatment. That is, the slide handling head 22 contacts against the bearing surface when the slide transport robot 18 moves the closure body 24 to the open position, by resisting the bias and then back to the closed position. Thus, after the slide 13 has been located in the slide treatment module 14 and the closure body 24 reverts to the closed position, the nozzle 26 of the probe 25 can then be lowered in the z axis to dispense reagents to the slide 13. It can also be seen that the slide treatment modules 14 are aligned in the apparatus 12 so as to be opened in the x direction to minimise the amount of movement for the slide transport robot 18 and the FTP robot 16.

FIGS. 6 to 9 show the probe 25 and the well 27 of the fluid transport system 10 in more detail. FIG. 5 shows the probe 25 without the well 27, where only the elongated body of the probe 25 is arranged to store reagents therein so as to prime the probe 25 with reagents. FIGS. 6 and 7 show the well 27 for further storing reagents to increase the volume of reagents to be primed to be dispensed. As described, the well 27 is a coiled tube of substantially similar diameter to the elongate tube of the body of the probe 25 to substantially increase the volume of reagents to be primed for dispensing to the slides 13 and to minimise the size of the probe 25. As described, the well 27 may take different forms, such as a tank, and need not be located at the end of the probe 25. For example, the well 27 could be a tank located at some point along the body of the probe 25.

Figure 9:
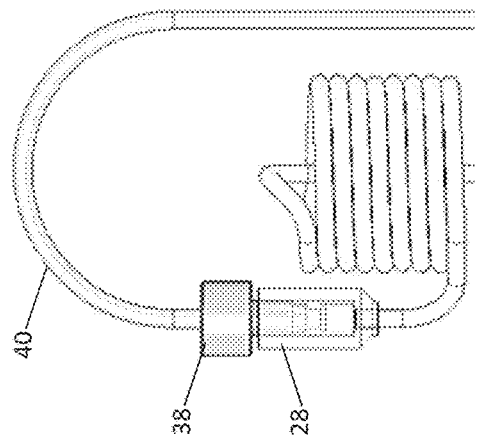
FIG. 9 is a front view of a connector for connecting a well of a fluid transport system to a reagent line according to an embodiment of the present invention.

The coiled tube of the well 27 is also removeably attached to a reagent line connected to the pumping means at a resealable connector 28. In FIG. 9, the connector 28 connects a flexible, tubular reagent line 40 to the well 27 via a plug 38 which creates a sealing fit with the connector 28. Furthermore, the body of the probe 25 is removeably attached to the FTP robot 16 using electrically insulating probe collars; specifically, a bottom collar in the form of a plastic collet 30 and a top collar in the form of a plastic clip 32 to hold the probe 25 in position and to insulate the probe 25 from the tubular rack 23.

Figure 8:
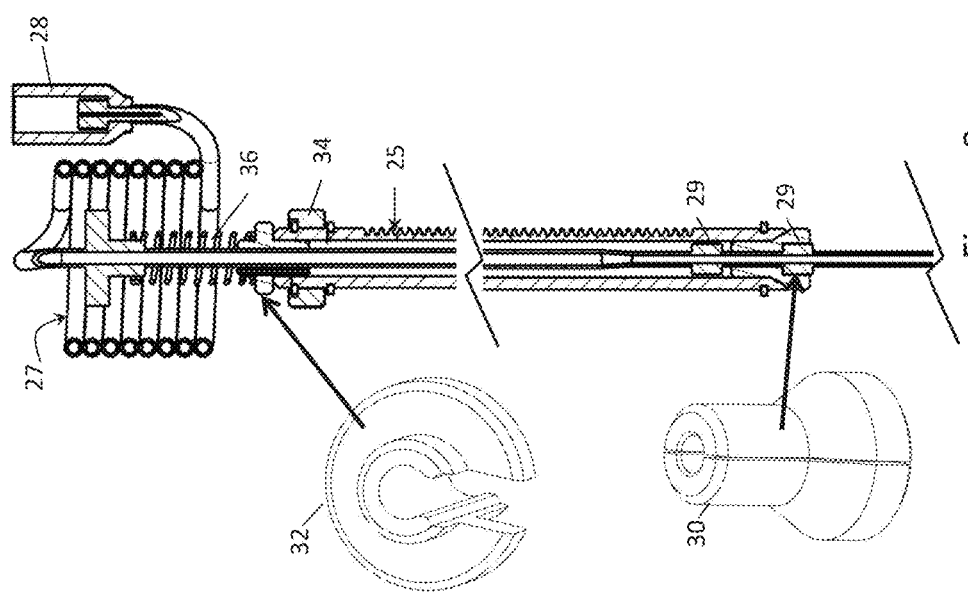
FIG. 8 is a sectional view of a probe of a fluid transport system showing collars for retaining the probe according to an embodiment of the present invention.

The probe 25 also has locating blocks 29 to locate and lock the probe 25 in the rack 23 using the collet 30 and the clip 32, as shown in more detail in FIG. 8. Here it can be seen that the probe 25 is mounted from the top of the tubular rack 23 and through the rack 23. A spring 36 and two plastic spacers locate and lock the probe 25 in position at the top of the rack 23. In addition, the rack 23 has a finger grip 34 arranged to slide relative to the rack 23 to remove the clip 32 from the rack 23 to remove the probe 25 from the rack 23. Also, the collet 30 is inserted into the gap between the tubular rack 23 and the probe 25 and held in place by the locating blocks 29 on the probe 25 to lock the probe 25 in position at the bottom of the rack 23.

Figure 13:
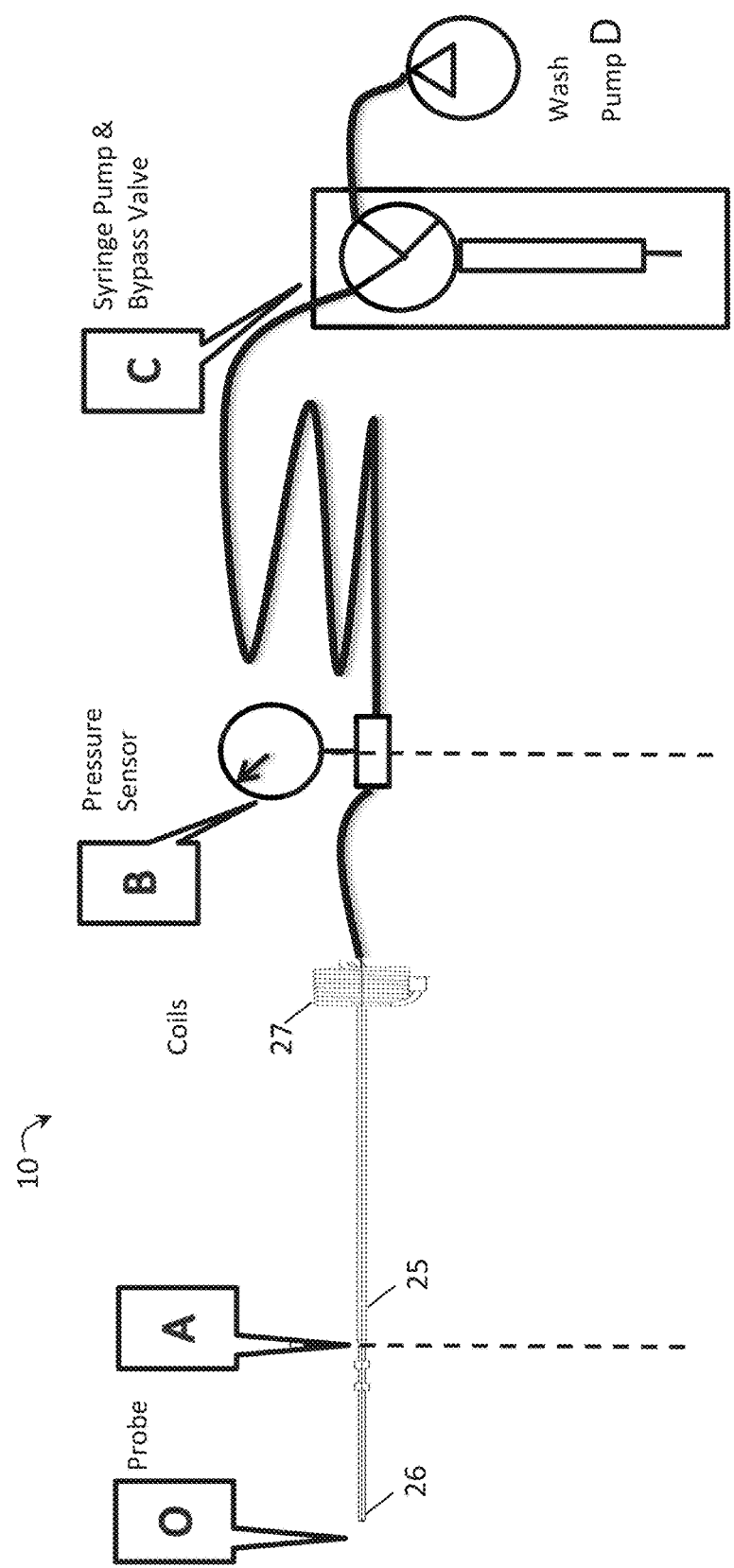
FIG. 13 is a schematic diagram of a fluid transport system according to an embodiment of the present invention.

FIG. 13 shows a schematic diagram of the fluid transport system 10 described above from the nozzle 26 of the probe 25 to the syringe pump C and, in this case, a wash pump D. It should be understood, however, that there may be multiple wash pumps D feeding into the syringe C which may also comprise a bypass valve. A reagent line extends between the well 27 of the probe 25 and the syringe pump C via a pressure sensor B. In an embodiment, the syringe C may be bypassed altogether by bypass valve C so that the one or more wash pumps D feed feed directly into the probe (see FIG. 12B). An example of the dimensions of the components of the system 10 with reference to this figure is as follows. From point O to A on the probe 25—that is, from the nozzle 26 to where the probe 25 is attached to the rack 23 of the FTP robot 16—the distance is 120 mm. The diameter of this dispensing end of the probe 25 from point O to A is 1.3 mm and the volume is 150 µl. The diameter of the body of the probe 25 from point A to the pressure sensor B and the diameter of the coiled tube of the well 27 is 2 mm. The length of tube of the well 27 combined with the length of the elongate body of the probe 25 volume is 1100 mm and the volume is 3500 µl. In the example, therefore, the amount of reagent primed to be dispensed in the body of the probe 25 and the well 27, as well as the reagent line to the pressure sensor, has a maximum volume of 3650 µl. The reagent line from the pressure sensor B to the syringe pump C is a plastic tube having a diameter of 2 mm and a length of 2500 mm. The length of the elongate body of the probe 25 enhances the provision of gaps, such as an air gap, to substantially separate different reagents drawn into the probe. This facilitates pumping and/or aspiration of more than one of the reagents from different ones of reagent containers successively with an air gap between successive reagents so as to prime the probe 25 with a plurality of different reagents. This allows the probe 25 to dispense at least two different reagents without returning to the reagent containers.

In an embodiment, the pressure sensor B senses pressure in the reagent line to confirm that reagents have been dispensed from the probe 25. It will be appreciated by those persons skilled in the art, however, that other sensing means for sensing dispensed reagent amounts can be employed by the system 10. For example, the sensing means is a liquid level sensor for sensing an amount of dispensed reagent from the probe 25. It will be appreciated that the liquid level sensor can be a capacitive liquid level sensor configured to monitor for changes in capacitance at the nozzle 26 of the probe 25 or it can be a pressure liquid level sensor configured to sense changes in pressure at the nozzle 26. Alternatively, optical liquid level sensing systems and ultrasonic systems may be employed.

In the embodiment where a capacitive liquid level sensor is employed by the system 10, the connector 28, clip 32 and collet 30 are made from an electrically insulating material, such as rubber or plastic, to electrically isolate the coiled tube and the body of the probe 25 from the other components of the FTP robot 16, such as the rack 23, so that the capacitive measurements can be made without interference from the other components.

Figure 10A:
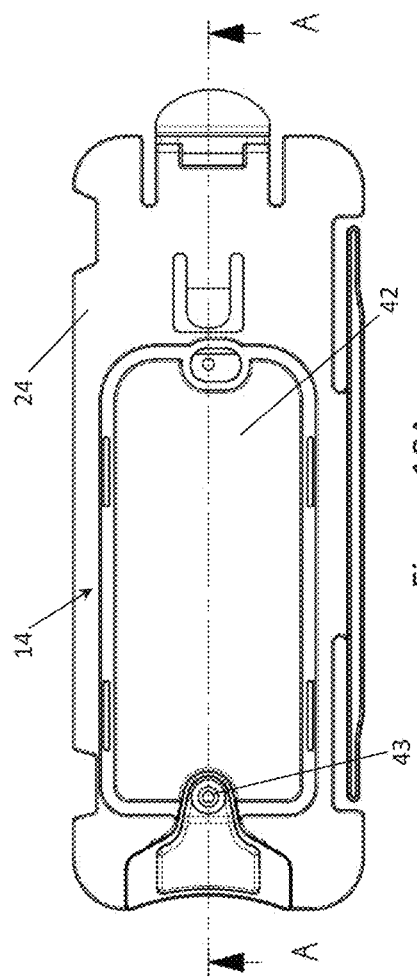
FIG. 10A is a top view of a cover member of a slide treatment module of an automated slide treatment apparatus according to an embodiment of the present invention.
Figure 10B:
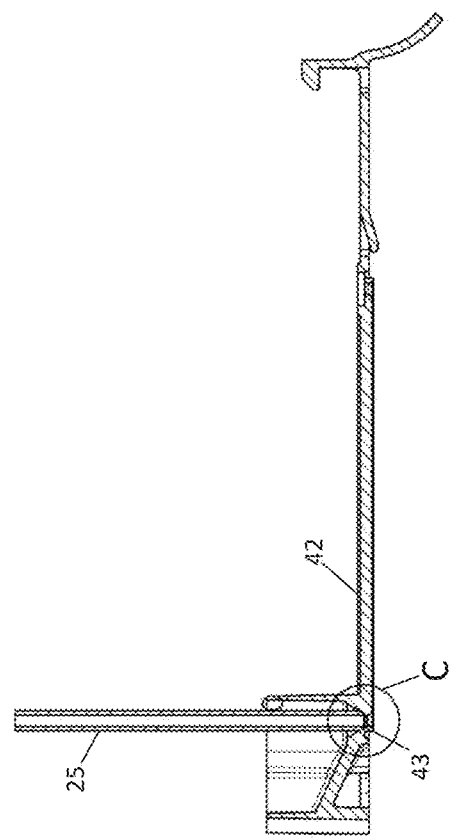
FIG. 10B is a sectional view taking along section AA of FIG. 10A of a probe of a fluid transport system coupling with the cover member of the slide treatment module of FIG. 10A.

Referring back to FIG. 10A and FIG. 10B, the closure body 24 of the slide treatment module 14 creates a sealed reaction chamber for treating tissue samples on the slide 13 with a cover member 42, shown in FIGS. 10A and 10B, of the slide treatment module 14. The cover member 42 is disposed on the underside of the closure body 24 and is arranged to form the sealed reaction chamber with the slide 13 when the closure body 24 is in the closed position after the slide transport robot 18 has located the slide 13 in the slide treatment module 14. Details of the cover member 42 are described in the co-pending U.S. provisional patent application entitled "Slide Staining Assembly and Cover Member". The FTP robot 16 and the BFR 15 can then dispense reagents to the slide 13 in the slide treatment module 14 when the closure body 24 is in the closed position in the designated order and with designated volumes to treat the tissue samples on the slides 13. It will be appreciated by those persons skilled in the art that the instructions for the designated reagents and the order that the reagents are to be dispensed can be stored in a memory in data communication with the controller.

Figure 11A:
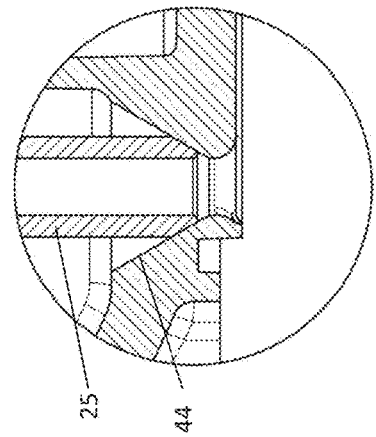
FIG. 11A is a sectional view of the probe and the cover member of FIG. 10B at section C.
Figure 11B:
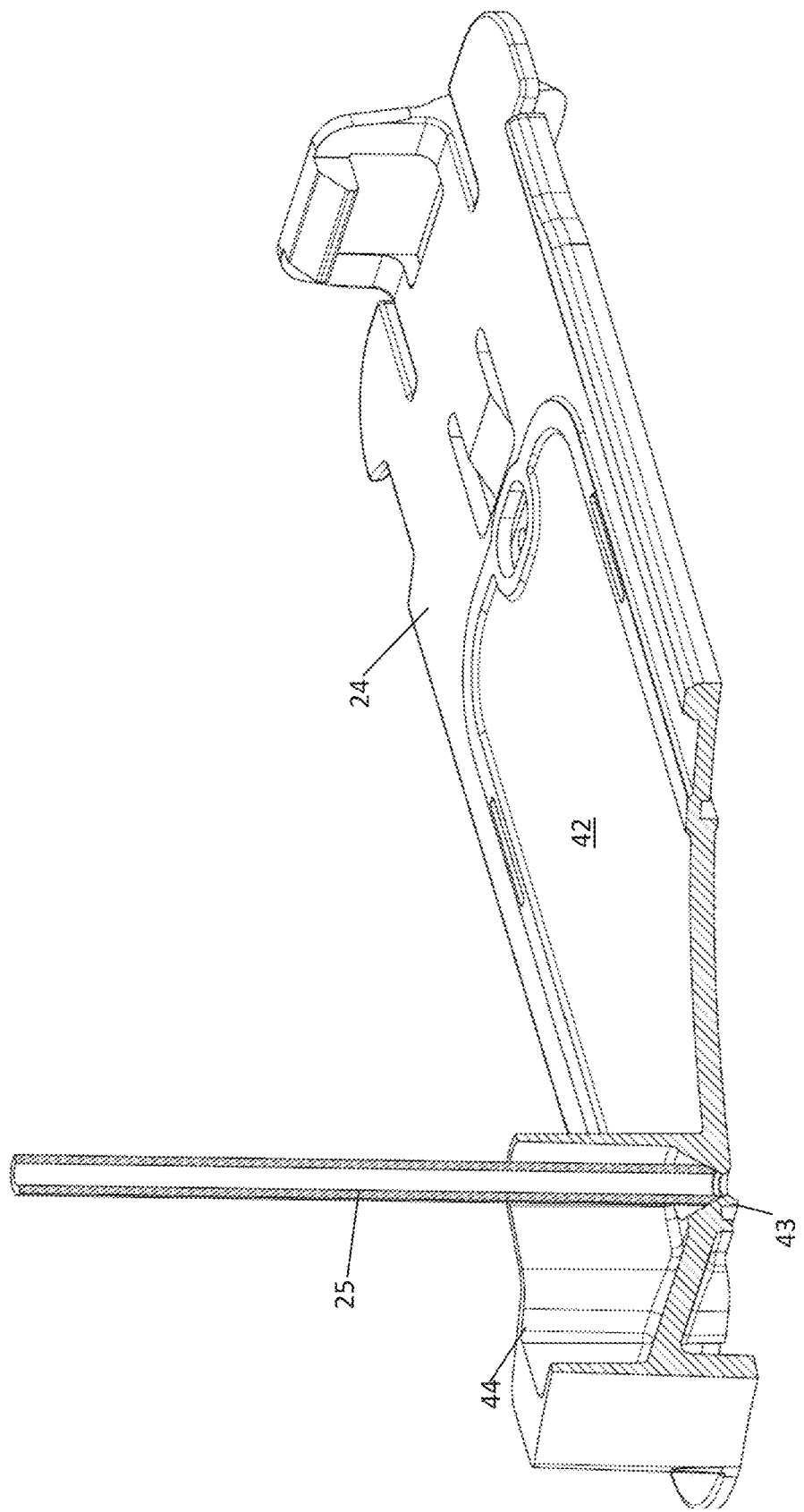
FIG. 11B is a cut away perspective view of the probe and the cover member of FIG. 10B.

The nozzle 26 of the probe 25 is arranged to couple with a receiving portion 44 of the cover member 42 in the slide treatment module 14, and substantially sealingly mate with an inlet port 43 in the receiving portion 44 of the cover member 42 whilst the reagents are being dispensed. Furthermore, the FTP robot 16 includes a driver means, such as the above described stepper motor, to urge the nozzle 26 of the probe 25 in the z axis towards the inlet port 43 of the slide treatment module 14 whilst the reagents are being dispensed to maintain a seal with the inlet port 43. For example, the driving means exerts a 5 to 30N force, such as, for example a 10N force on the probe 25 to urge the nozzle 26 of the probe 25 towards the inlet port 43 using a stepper motor in constant torque mode. It can be seen in FIGS. 11A and 11B that the inlet port 43 may have a chamfer, such as 30 to 75 degree, for example a 60 degree chamfer to guide and to seal with the nozzle 26 of the probe 25.

Referring back to FIG. 1 and to FIGS. 12A and 12B, the apparatus 12 includes a wash drum 49 of a wash station 48 for washing the probe 25 when the probe is inserted into the wash drum 49 of the wash station 48 via movement of the FTP robot 16 as described above. Furthermore, as shown in FIG. 13, the syringe pump C is connected to the wash pump D via a wash line so that the reagent lines of the FTP robot 16 can be washed with wash fluid, such as Bond™ wash, DI water and alcohol pumped from the wash pump D. The wash pump D may be supplied by a fluid delivery line suitable for the delivery of fluids, such as hydraulic fluid or fluids, including, but not limited to one or more of wash solution, water, buffer, diluent such as antibody diluent, cleaning solution and the like. In one embodiment, the wash pump may be supplied by a plurality of fluid delivery lines suitable for the delivery of fluids.

In one embodiment, the wash pump D is configured to pump wash fluid to a wash fluid injection port 50 by the controller from one or more wash fluid containers. The wash fluid then passes over a textured surface 52 to create a turbulent flow of the wash fluid over the probe 25 when it is inserted into the wash drum 49. It can be seen that the textured surface 52 includes spiral corrugations in the wash drum in the form of a spiral wash rings to create the turbulent flow to wash the probe 25. The wash drum 49 also includes a collection chamber 54 and scavenging port 56 to collect and remove the wash fluid from the wash drum 49. It will be appreciated by those persons skilled in the art that the wash fluid may be recycled and reused by the wash pump.

In the embodiment shown in FIG. 12 B, the wash drum 49 includes an inlet port 55 and an outlet port 57 for circulating air past the nozzle 26 of the probe 25 to improve the washing process. In this case, a vacuum means is applied to the outlet port 57 so that air is drawn out of the outlet port 57 and in through the inlet port 55 so that it travels around the probe 25 when it is inserted into the wash drum 49. The air is forced though the inlet port from the atmosphere in this embodiment. Seal 60 prevents air from being drawn into the wash drum 49 around probe 25. Thus, in use, for example, wash fluid is injected via probe 25 into the wash drum 49 using the wash pump D and the vacuum is applied so that air from the inlet port 55 mixes with the wash fluid around the probe 25 to aid in cleaning the probe 25. It will be appreciated by those persons skilled in the art, however, that a closed system could be employed to wash the probe 25 and, for instance, a captive inert gas is used instead of air.

Figure 14:
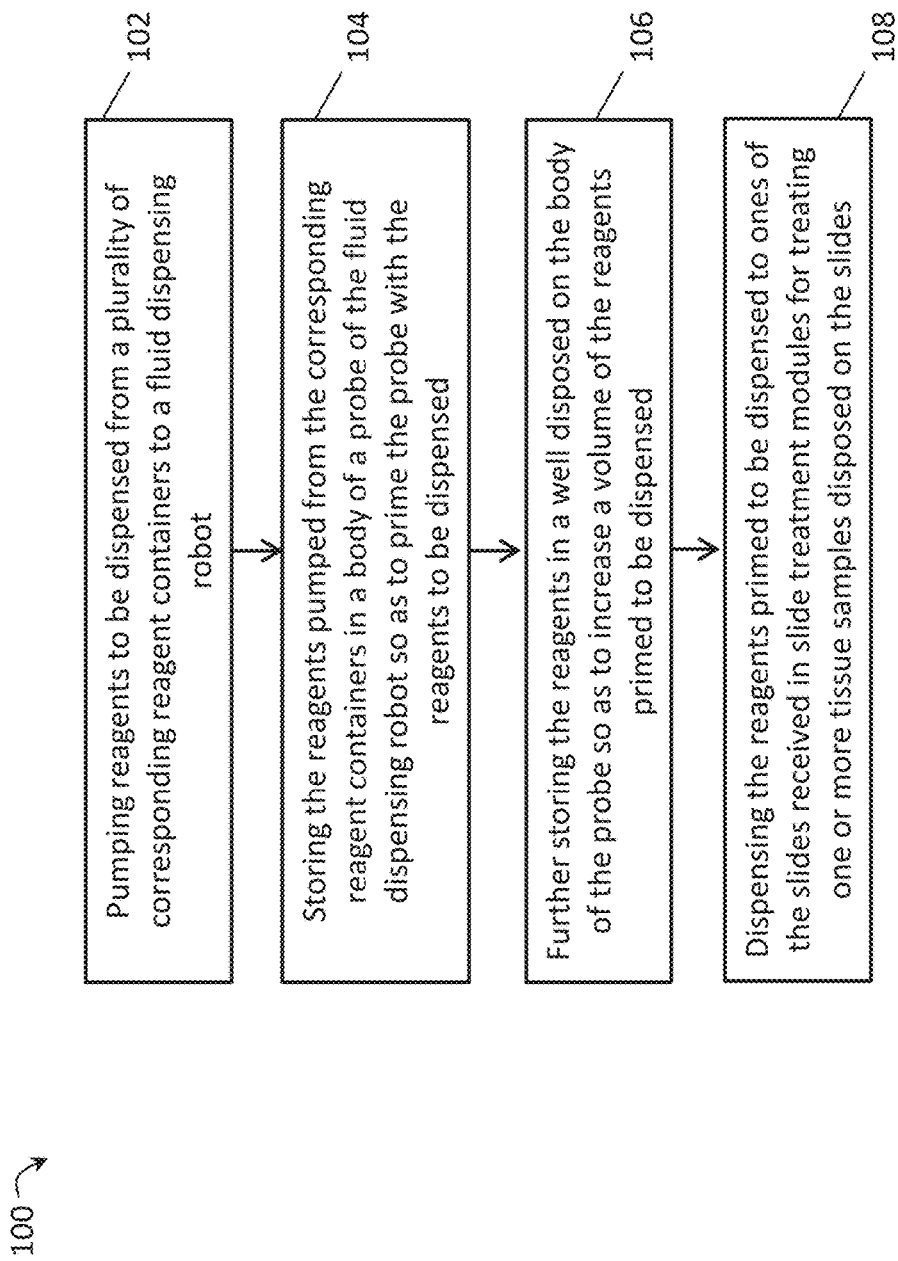
FIG. 14 is a flow chart of a method of dispensing reagents for treatment of tissue samples disposed on slides according to an embodiment of the present invention.

Referring now to FIG. 14, there is shown a summary of a method 100 of transporting fluid for treatment of one or more tissue samples disposed on slides, whereby ones of the slides are received in a plurality of slide treatment modules and a plurality of fluid reagents are dispensed by at least one fluid dispensing robot to the slides received in the slide treatment modules to treat the tissue samples on the slides. The method 100 includes the steps of pumping 102 the reagents to be dispensed from a plurality of corresponding reagent containers, storing 104 one or more of the reagents pumped from the corresponding reagent containers in a body of a probe so as to prime the probe with said one or more of the reagents to be dispensed, further storing 106 said one or more of the reagents in a well disposed on the body of the probe so as to increase a volume of the one or more of the reagents primed to be dispensed, and dispensing 108 said one or more of the reagents primed to be dispensed to the slides received in the slide treatment modules.

Further aspects of the method will be apparent from the above description of the fluid transport system 10. A person skilled in the art will also appreciate that a method could be embodied in a program code. The program code could be supplied in a number of ways, for example on a tangible computer readable medium, such as a disc or a memory.

It is to be understood that various alterations, additions and/or modifications may be made to the parts previously described without departing from the ambit of the present invention, and that, in the light of the above teachings, the present invention may be implemented in software, firmware and/or hardware in a variety of manners as would be understood by the skilled person.

The discussion of documents, acts, materials, devices, articles and the like is included in this specification solely for the purpose of providing a text for the present invention. It is not suggested or represented that any of these matters formed part of the prior art base or were common general knowledge in the field relevant to the present invention as it existed before the priority date of each claim of this application.

Where the terms "comprise, "comprises", "comprised" or "comprising" are used in this specification (including the claims) they are to be interpreted as specifying the presence of one or more features, but not precluding the presence or addition of further features in various embodiments of the invention.

The invention claimed is:

1. A fluid transport system for treating one or more tissue samples disposed on slides, comprising:
    an automated slide treatment apparatus including a plurality of slide treatment modules arranged to each receive one of the plurality of slides;
    a fluid dispensing robot configured to dispense a plurality of reagents to each one of the slides received in the slide treatment modules to treat said one or more tissue samples respectively,
    wherein the fluid dispensing robot includes:
        a pumping means configured to pump the reagents to be dispensed from a plurality of corresponding reagent containers;
        a probe having a body arranged to store one or more of the reagents pumped via the pumping means so as to prime the probe with said one or more of the reagents to be dispensed;
        a well disposed on the body of the probe and arranged to store further of said one or more of the reagents so as to increase a volume of the one or more of the reagents primed to be dispensed; and
    a driver means for the probe; wherein
    the probe is arranged to dispense said one or more of the reagents primed to be dispensed to each one of the slides received in the slide treatment modules,
    the fluid dispensing robot includes a nozzle disposed at an end of the probe and arranged to dispense said one or more of the reagents primed to be dispensed,
    the slide includes a cover member with an inlet port,
    the nozzle of the probe is arranged to couple with a chamfered opening of the cover member in said one of the slide treatment modules and substantially sealingly mate with the inlet port of said cover member while said one or more reagents are being dispensed,
    the driver means continuously urges the nozzle of the probe towards the inlet port of said one of the slide treatment modules while the one or more reagents are being dispensed to maintain the seal with the inlet port, and
    the probe and an interior of the slide treatment module are exposed to an ambient atmosphere prior to being sealingly mated.

2. A system as claimed in claim 1, wherein the well and the body of the probe are removably attached to a reagent line connected to the pumping means at a resealable connector.

3. A system as claimed in claim 1, wherein the body of the probe is removably attached to the fluid dispensing robot at one or more probe collars.

4. A system as claimed in claim 1, wherein the fluid dispensing robot further includes a pressure sensor disposed between the well and the pumping means for sensing an amount of dispensed reagent from the probe.

5. A system as claimed in claim 1, wherein the fluid transport system further includes a wash station for washing the probe when the probe is inserted in a wash drum thereof.

6. A system as claimed in claim 5, wherein the wash drum includes a wash fluid injection port connected to a wash pump of the fluid transport system, wherein the wash pump is configured to pump wash fluid into the wash drum from one or more wash fluid containers.

7. A system as claimed in claim 6, wherein the wash drum has a textured surface to create a turbulent flow of said wash fluid over the probe when inserted into the wash drum.

8. A system as claimed in claim 6, wherein the wash drum further includes a collection chamber and scavenging port to collect and remove said wash fluid from the wash drum.

9. A system as claimed in claim 5, wherein the wash drum includes an inlet port and an outlet port whereby a gas enters the wash drum through the inlet port to mix with the wash fluid around the probe and the gas exits through the outlet port.

10. A system as claimed in claim 9, further including a vacuum means arranged to apply a vacuum force to the outlet port to draw gas into the inlet port and out of the outlet port.

11. A system as claimed in claim 1, wherein the pumping means is further configured to pump and/or aspirate more than one of the reagents from different reagent containers successively with an air gap between successive reagents so as to prime the probe with a plurality of different reagents.

12. A system as claimed in claim 1, wherein the driver means includes a stepper motor having a constant torque mode.

13. A method of transporting fluid for treatment of one or more tissue samples disposed on slides whereby each one of the slides are received in a plurality of slide treatment modules, the plurality of slide treatment modules each including a cover member having a chamfered opening, and a plurality of reagents are dispensed by at least one fluid dispensing robot to each one of the slides received in the slide treatment modules to treat said one or more tissue samples respectively, the method comprising:
    pumping the reagents to be dispensed from a plurality of corresponding reagent containers;
    storing one or more of the reagents pumped from the corresponding reagent containers in a body of a probe so as to prime the probe with said one or more of the reagents to be dispensed;
    further storing said one or more of the reagents in a well disposed on the body of the probe so as to increase a volume of the one or more of the reagents primed to be dispensed; and
    dispensing said one or more of the reagents primed to be dispensed to each one of the slides received in the slide treatment modules via a nozzle disposed at an end of the probe, whereby the nozzle of the probe is arranged to couple with the chamfered opening of the cover member in said one of the slide treatment modules and substantially sealingly mate with an inlet port of said cover member while said one or more reagents are being dispensed, wherein
    the nozzle of the probe is continuously urged towards the inlet port of said one of the slide treatment modules while the one or more reagents are being dispensed to maintain the seal with the inlet port, and
    the probe and an interior of the slide treatment module are exposed to an ambient atmosphere prior to being sealingly mated.

14. Computer program code which when executed by a controller implements the method of claim 13.

15. A tangible computer readable medium comprising the program code of claim 14.

* * * * *